United States Patent
Brisken et al.

(10) Patent No.: US 6,464,680 B1
(45) Date of Patent: Oct. 15, 2002

(54) ULTRASONIC ENHANCEMENT OF DRUG INJECTION

(75) Inventors: Axel Brisken, Fremont, CA (US); Robert Zuk, Atherton, CA (US); John McKenzie, San Carlos, CA (US); Jeff Isner, Weston, MA (US); Meno Nassi, Palo Alto, CA (US)

(73) Assignee: Pharmasonics, Inc., Sunnyvale, CA (US)

( * ) Notice: Subject to any disclaimer, the term of this patent is extended or adjusted under 35 U.S.C. 154(b) by 0 days.

(21) Appl. No.: 09/126,011

(22) Filed: Jul. 29, 1998

(51) Int. Cl.⁷ .............................................. A61M 31/00
(52) U.S. Cl. ...................... 604/501; 604/511
(58) Field of Search .......................... 604/22, 28, 511, 604/500, 501, 522, 518; 128/898

(56) References Cited

U.S. PATENT DOCUMENTS

| | | | | |
|---|---|---|---|---|
| 5,197,946 A | * | 3/1993 | Tachibana | 604/22 |
| 5,490,840 A | * | 2/1996 | Uzgris et al. | 604/22 |
| 5,658,247 A | * | 8/1997 | Henley | 604/20 |
| 5,752,515 A | * | 5/1998 | Jolesz et al. | 604/22 |
| 6,066,123 A | | 5/2000 | Li et al. | |

FOREIGN PATENT DOCUMENTS

| WO | WO 97/40679 | 11/1997 |
|---|---|---|
| WO | WO 00/18468 | 4/2000 |

OTHER PUBLICATIONS

Bednarski et al., "In vivo target–specific delivery of macromolecular agents with MR–guided focused ultrasound" Radiology (1997) 204(1):263–268.

Machluf et al., "A novel vector for gene transfection using ultrasound energy" (1998) Pediatrics 102(3):844 Abstract No. 43.

Tsurumi, MD, Yukio et al., Direct Intramuscular Gene Transfer of Naked DNA Encoding Vascular Endothelial Growth Factor Augments Collateral Development and Tissue Perfusion, *Circulation*, 94:12: 3281–3290 (Dec. 15, 1996).

Enhancing Cell Transformation: The SonoPorator 100, Product Literature.*

* cited by examiner

*Primary Examiner*—Manuel Mendez
*Assistant Examiner*—Michael M Thompson
(74) *Attorney, Agent, or Firm*—Townsend and Townsend and Crew LLP

(57) ABSTRACT

A method of enhancing cellular absorption of a substance delivered into a target region of a patient's body, comprising: (a) delivering the substance to the target region; and (b) directing vibrational energy to the target region, wherein the vibrational energy is of a type and in an amount sufficient to enhance absorption into cells of the target region.

21 Claims, 19 Drawing Sheets

ULTRASONIC ENHANCEMENT OF DRUG INJECTION

TECHNICAL FIELD

The present invention relates to methods and devices for enhancing cellular absorption of a substance delivered into a target region of a patient's body.

BACKGROUND OF THE INVENTION

A current standard technique for the delivery of drugs or other substances into the human body is needle injection. A bolus containing the drug is typically injected into muscle or fatty tissue and is then absorbed into the interstitial fluid or directly into the fatty tissue. Over a period of time, the vascular system of the body takes over and flushes the drug out of the interstitial fluid or fat and into the capillaries. From there, the cardiovascular system widely distributes the drug into the rest of the patient's body.

Newly developed drugs often have application only to specific organs or sections of organs. As such, systemic distribution of the drug throughout the remainder of the body can: (1) dilute very expensive drugs, weakening their effects, (2) generate an effect systemically instead of locally, and (3) widely distribute a drug which may be toxic to other organs in the body. Furthermore, some of the newly developed drugs include DNA in various forms, such DNA being degraded very rapidly by natural mechanisms in the body if delivered systemically, thus preventing a full dose from reaching the designated organ. Accordingly, it would be desirable to provide devices, kits, and methods for delivering such site-specific drugs in a manner which enhances absorption specifically at the site of their delivery into a target region of a patient's body.

SUMMARY OF THE INVENTION

The present invention provides methods, devices, and kits for enhancing cellular absorption of a drug or other substance into a local target region of a patient's body, thereby avoiding the undesirable effects of the substance being widely dispersed throughout the patient's body by the patient's cardiovascular system. By "cellular absorption," it is meant that at least a significant proportion of the total amount of drug delivered to the site is absorbed or otherwise taken up by the cells within or surrounding the target site. The nature of the cells will vary depending on the target site. The cells may be muscle or fat cells receiving transcutaneous, intraoperative, or percutaneous injection. In a preferred aspect of the present invention, these cells comprise the patient's myocardial tissue. However, the cells may also be endothelial, epithelial, and/or other cells which line the interior or exterior of target organs, or brain cells protected by the blood/brain barrier, or organ cells in general. Lastly, the cells may also be specific organ cells of a target organ.

Specifically, a method is provided for enhancing cellular absorption of a substance, comprising the steps of: (a) delivering the substance to the target tissue region, and (b) directing vibrational energy to the target region, wherein the vibrational energy is of a type and amount sufficient to enhance absorption of the substance into the cells of the target region. In a preferred aspect of the present invention, the vibrational energy has a mechanical index in the range of 0.1 to 20 and a thermal index the range of 0.001 to 4.0. Devices for emitting ultrasonic vibrations of a type and amount sufficient to enhance cellular absorption may comprise a wide variety of known transducer systems, such as piezoelectric and magnetostrictive devices.

The application of such vibrational energy to the target region increases cellular absorption on the order of 5 to 5,000 percent or more for biological reporters such as luciferase gene beta-galactosidase and for drugs such as heparin, probucol, the family of anti-cancer vectors, liposome-complexed plasmid DNA, adeno-associated virus, vascular endothelial growth factors, and naked DNA relative to their uptake in the absence of the vibrational energy.

The present invention will be useful for delivering a wide variety of drugs and other substances to target tissue sites. The substances will usually have a pharmological or biological effect and range from those generally classified as small molecule drugs (usually below 2 kD, more usually below 1 kD), such as hormones, peptides, proteins, nucleic acids, carbohydrates, and the like to those generally classified as large molecule drugs (usually above 200 kD) such as complete strands of DNA. The present invention will be particularly effective in delivering macromolecules such as biologically active proteins and nucleic acids. For delivery to the muscles in general, or the myocardium in particular, useful substances may enhance angiogenesis stimulators, such as vascular endothelial growth factor (VEGF) and basic fibroblast growth factor (BFGF). Other useful substances my include endothelial nitric oxide synthase (eNOS) for inhibiting restenosis, and brain naturatic peptides, and beta-adrenogenic receptors for preventing congestive heart failure. Ultrasound in combination with DNA-based vaccines would enhance protein expression by improving the humoral and cellular immune response.

In a preferred method, the substance is delivered to the target cells. This delivery can be accomplished transcutaneously or percutaneously by way of an injection needle or needles, injected in high-velocity, small-volume jets of delivery fluid, or delivered interoperatively. The substance can also be delivered by a controlled release device such as a microsphere. Substance delivery could also be accomplished by positioning the distal end of a delivery device such as a catheter or hand held device proximal to a target region of tissue, wherein a vibrational energy emitter also being positioned at the distal end of the device. For delivery through the skin or surgical use, the device may be constructed similarly to a syringe having an ultrasonic driver on or near the needle tip. For internal delivery, the device will typically be formed as a catheter for intraluminal or endoscopic introduction to a target site.

By "delivery," it is meant that the drug or other substance is injected or otherwise physically advanced into a target region of tissue. Injection can be performed with a needle and a pressurized source of the substance, e.g. a syringe. A controlled delivery device or depot containing the drug could also be implanted within the target tissue. Substances of interest will typically be delivered through the internal walls and membranes of organs (particularly the epicardium and endocardium when targeting the myocardium), blood vessels, and the like, as well as through the skin. In some instances, the catheter will be percutaneously introduced to a blood vessel or open body cavity in order to permit access to the internal organs and delivery sites.

The present invention also provides a device for enhancing cellular absorption of a substance delivered to a target tissue region of a patient's body comprising a substance delivery system and a vibrational energy emitter which is adapted to emit vibrational energy of a type and amount sufficient to enhance cellular absorption at or proximal to the tissue surface. Preferably, the substance delivery system comprises one or more injection needles.

In one embodiment, the injection needle and the ultrasound energy emitter form a small integrated device which is received at the distal end of a catheter. In one aspect of this embodiment, the energy emitter may include one or more vibrational energy emitting transducers received within the injection needle. In various embodiments, the vibrational energy emitter is disposed proximate to the substance delivery system. In certain preferred embodiments, the vibrational energy emitter is mounted directly to the injection needle. The vibrational energy emitter may also be disposed concentrically around the substance delivery system. Specifically, the substance delivery system may comprise an injection needle and the vibrational energy emitter is mounted directly on the injection needle. In various embodiments, the injection needle system comprises a plurality of retractable radially extending injection needles which are positioned at the distal end of a catheter such that when the catheter is received into an intraluminal cavity, the injection needles can be radially extended outward puncturing the wall of the cavity and entering into the underlying tissue. In various preferred embodiments, the vibrational energy emitter emits vibrational energy laterally outward in radial directions away from the distal end of a catheter such that the catheter can be positioned in parallel orientation to the target tissue, such as when the distal end of the catheter is received in a blood vessel or other luminal cavity.

Also, specific embodiments of the present invention may include additional diagnostic, measurement, or monitoring components or capabilities. For example, the device for emitting vibrational energy to the target region may be adapted to detect the net electromechanical impedance of the target tissue in opposition with the vibrational device thus enabling an operator to determine when the distal end of the device contacts the target tissue by observing a change in the effective impedance of the device. Moreover, an echo ranging transducer positioned on the distal end of the catheter or other device can be used to determine the thickness and condition of the target tissue. This can be accomplished by operating the ranging transducer in a pulse echo mode, and characterizing the amplitude, spectral content, and timing of the returning echoes. Furthermore, an electrocardiograph monitoring electrode can optionally be positioned on the distal end of the catheter adjacent the substance delivery system for monitoring potentials in a patients myocardium. This can be useful for providing therapy to the site in the myocardium which is responsible for rhythm abnormalities.

Kits according to the present invention may comprise the delivery devices in combination with instructions for use setting forth any of the above-described methods.

DESCRIPTION OF THE PREFERRED EMBODIMENT

The present invention provides a method for enhancing cellular absorption of a drug or other substance into a local target region of a patient's body, thereby avoiding the undesirable effects of the substance being widely dispersed throughout the patient's body by the patient's cardiovascular system or having the substance compromised by the natural cleansing activities of the patients organs, as follows.

First, the substance is delivered to the target region of a patient's tissues. Secondly, vibrational energy is directed to the target region, wherein the vibrational energy is of a type and amount sufficient to enhance absorption of the substance into the cells of the target region, as will be explained.

Figure 1:
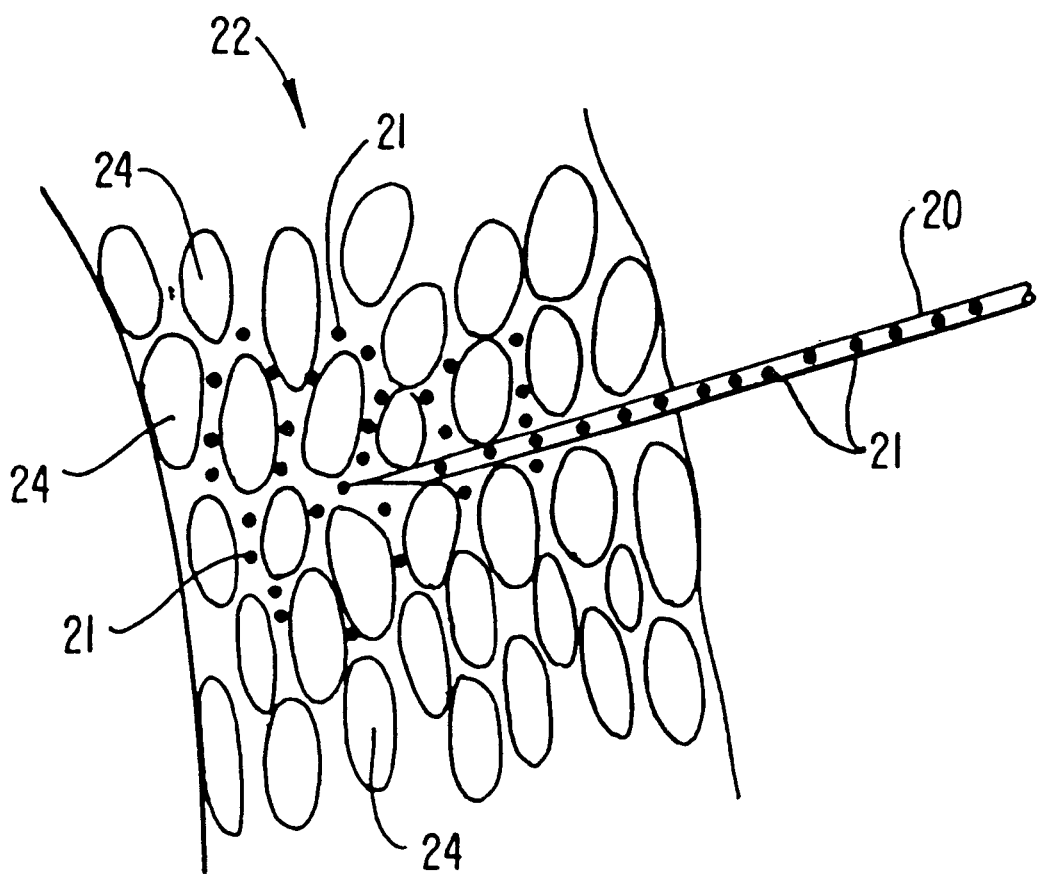
FIG. 1 shows a microscopic pictorial representation of a substance being injected into a target tissue by way of an injection needle.

FIG. 1 illustrates an injection needle 20 delivering a drug or other substance 21 into a region of target tissue 22 which is comprised of a plurality of cells 24. In the absence of the present invention's application of vibrational energy, drug 21 will tend to absorb slowly into cells 24 causing the drug 21 to be distributed widely in the patient's body thus either diluting a very expensive drug and thereby weakening its effect or generating a systemic effect on the patient instead of the desired local effect.

Figure 2:
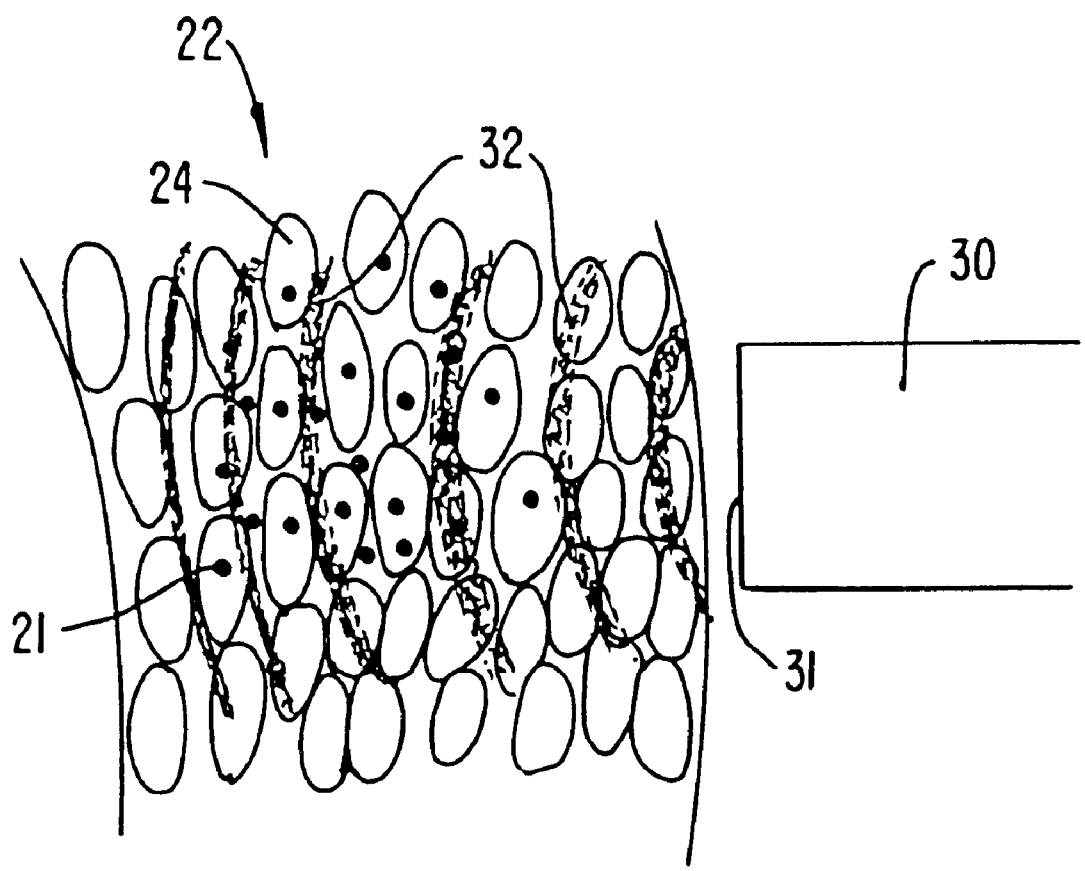
FIG. 2 is a microscopic pictorial representation of cellular absorption of the substance of FIG. 1 mediated by ultrasound energy.

However, in accordance with the present invention as shown in FIG. 2, a vibrational emitter 30, may be used to emit ultrasound waves 32 into the target tissue 22 in a type and in an amount sufficient such that drug 21 is instead readily absorbed into cells 24. As will be explained herein, emitter 30 preferably has a vibrational energy with a mechanical index in the range of 0.1 to 20 and a thermal index in the range of 0.001 to 4.0. In addition, this vibrational energy preferably has a frequency range of 20 kHz to 3.0 MHz.

The bio-effects of ultrasonic energy are typically mechanical in nature (cavitational or pressure effects) or thermal in nature (heat due to absorption of energy or energy conversion). The American Institute for Ultrasound in Medicine (AIUM) and the National Electrical Manufacturers Association (NEMA) in "Standard for Real-Time Display of Thermal and Mechanical Indices on Diagnostic Ultrasound Equipment", 1991, have together defined the terms "mechanical index" and "thermal index" for medical diagnostic ultrasound operating in the frequency range of 1 to 10 MHz, as follows:

Mechanical index, (hereafter "MI"), is defined as the peak rarefactional pressure (in Mpa) at the point of effectivity (corrected for attenuation along the beam path) in the tissue divided by the square root of the frequency (in MHz), or $$MI = P(\text{Mpa})/\text{sqrt}(f[\text{MHz}])$$

The tolerated range for diagnostic imaging equipment is up to an MI of 1.9. MI values over 1 to 2 represent acoustic levels which can cause mechanical bio-effects.

Thermal index, (hereafter "TI"), is defined as the energy (in mW) times the frequency (in MHz), divided by the constant 210, or $$TI = W(\text{mW}) * f(\text{MHz})/210$$

A TI of 1 implies a temperature increase in normal vascularized muscle tissue of one degree Centigrade. The FDA standard for a maximum temperature of surface contact ultrasound devices is 41 degrees C. "Deep heat" ultrasound therapy devices may generate higher temperatures in tissue. In the vascular arena, however, even slight temperature excursions may cause unwanted formation and accumulation of clot. Moreover, increased temperatures of tissue may cause inflammation in the area of treatment. Therefore, TI values in excess of 1 to 2 are generally considered the threshold for causing undesirable bio-effects.

A "therapeutic window" occurs within the range of ultrasound energy generally above the level used for diagnostic purposes, and below the level where profound tissue damage occurs. As described above, standards exist for characterization of mechanical and thermal energy. MI and TI resp., associated with ultrasound energy, and well known limits exist for diagnostic ultrasound. Mechanical and thermal indices above diagnostic limits are regarded as potentially damaging to tissue, and are exploited by various therapeutic devices for tissue destruction, ablation, and deep heating. These therapeutic devices typically specify operating conditions based on frequency (kHz or MHz) and intensity (W/cm2). As defined above, both MI and TI effects embody frequency and intensity, and therefore for the purpose of this invention, ultrasound conditions will he specified solely in terms of MI and TI.

In an aspect of the present invention, ultrasound conditions which favor a high mechanical index and a low thermal index induce a preferred cellular response which promotes increased porosity and subsequent uptake of therapeutic agents. In accordance with the present invention, a preferred range for enhanced drug delivery is an MI of 0.1 to 20 and a TI of 4 or less, and more preferably, a MI of 0.3 to 15 and a TI of less than 4, still more preferably a MI of 0.5 to 10 or TI less than 4, and most preferably a MI of 0.5 to 5 and a TI of less than 4. A mechanical index greater than 20 can cause excessive membrane damage and cell necrosis due to inertial cavitation, microstreaming, or radiation pressure. Moreover, a thermal index greater than 4 can cause significant heating of the tissue resulting in denaturation and necrosis. By virtue of controlled mechanical action on the tissue interfaces and cellular membranes, temporary disruption of membranes occurs, thereby increasing porosity and perfusion of adjacent liquids into cells. Ultrasound induced membrane disruption has moderate durability, with most cells returning to normal. In accordance with an aspect of the present invention, controlled disruption of membranes allows therapeutic agents to more readily pass into the cells and cell organelles including the nucleus. An advantage of this system is its improvement in the efficiency of gene transfection and subsequent expression of genes.

In contrast to the present invention, existing ultrasound transducers used for diagnostic purposes are typically highly damped, have low sensitivity, and have a broad bandwidth response. Such transducers are designed to generate very short ultrasound pulses and to receive highly complex and irregular return echoes which are used to generate images or other diagnostic information. These transducers are capable of generating a high thermal index when operated at a high duty cycle (ie: the fraction of time during which the ultrasound field is energized) such as greater than 50%, but are incapable of generating a high mechanical index, primarily because of their high operating frequency (3 MHz and above) and heavy damping. As the above equation for MI indicates, at constant pressure, MI decreases by the square root of frequency. Accordingly, these diagnostic device transducers cannot generate enough pressure (amplitude) to overcome the frequency related loss. These restrictions apply to transcutaneous as well as intravascular diagnostic ultrasound devices.

Ultrasound transducers used for therapeutic purposes generally fall into two categories: thermal devices having high frequency for thermal effects, ie. deep heating, and mechanical devices having low frequency for mechanical effects, ie. lithotripsy and clot lysis.

Thermal devices are used transcutaneously for deep heating and tissue destruction, invasively for destroying pathological tissue, and percutaneously for ablation. In contrast to the present invention, these devices operate at a high duty cycle (greater than 50%) and high thermal index (greater than 4). Similar to the existing ultrasonic diagnostic transducers, ultrasonic therapeutic transducers are generally incapable of operating with a high mechanical index due to their high operating frequency and heavy damping.

Mechanical devices for lithotripsy, or disintegration of concretions within the body, are exclusively transcutaneous and not invasive. They operate at low frequency (20–500 kHz) and have very large acoustic apertures which allow the ultrasound energy to be focussed within the body. By virtue of their frequency and application, these devices operate with a high mechanical index and low thermal index. Clot lysis using low frequency ultrasound energy is achieved by positioning a transducer external to the body and percutaneously transferring vibrational energy into veins and arteries through a translating wire coupled to the transducer. These devices suffer from high frictional power loss when used in curved arteries and lumens.

In the present invention, vibrational energy emitters capable of high MI and low TI coupled to a substance delivery device which can be used transcutaneously or intraoperatively in the form of a hand held probe or injection device, and percutaneously in the form of a catheter are provided.

In the present invention, the application of vibrational energy to the target region increases cellular absorption on the order of 5% to 5,000% or more for drugs such as hormones, peptides, proteins, nucleic acids, carbohydrates, DNA vaccines, and angiogenesis stimulators relative to their uptake in the absence of such vibrational energy. For example, cellular transfections (DNA transfer into the nucleus of the cell, as manifested by altered expression of the cell) of a reporter gene Beta galactosidase into muscle tissue has been shown to increase by over a factor of 50 at an MI of 0.05 to 5.0.

In preferred embodiments, emitter 30 has a generally planar vibrational surface 31 which is positioned proximate to, or engages, a surface of target tissue 22, such as the external surface of the patient's skin or an external surface of an organ comprising target tissue 22.

The step of delivering the substance 21 by way of injection needle 20 or otherwise can be accomplished either prior to, concurrently with, or after the step of directing vibrational energy emitted by emitter 30 to cells 24 of target region 22 as is shown in FIG. 2. In an alternative method, the step of delivering substance 21 into target region 22 can be accomplished by forming an incision in the patient's skin and depositing the substance 21 (e.g. in the form of an implantable release depot) into the incision.

In preferred embodiments, target region 22 can be the myocardium of the patient and substance 21 can be any substance which promotes angiogenesis, for example VEGF, BFBF, and the like, and their corresponding genes. It is to be understood, however, that target region 22 is illustrative of any target tissue region in the patient's body and substance 21 is illustrative of any of a variety of drugs or other substances which have therapeutic effect upon a local region of the patient's tissues. For example, substance 21 can include any drug useful in the treatment of vascular diseases, including proteins, such as growth factors, clotting factors, clotting factor inhibitors; nucleic acids, such as the genes which encode the listed proteins, antisense genes, and the like. It may also include chemotherapeutic agents for the treatment of cancer and other hyperproliferative diseases; and may also include vaccines and any other type of proplactive substance or agent.

Figure 3A:
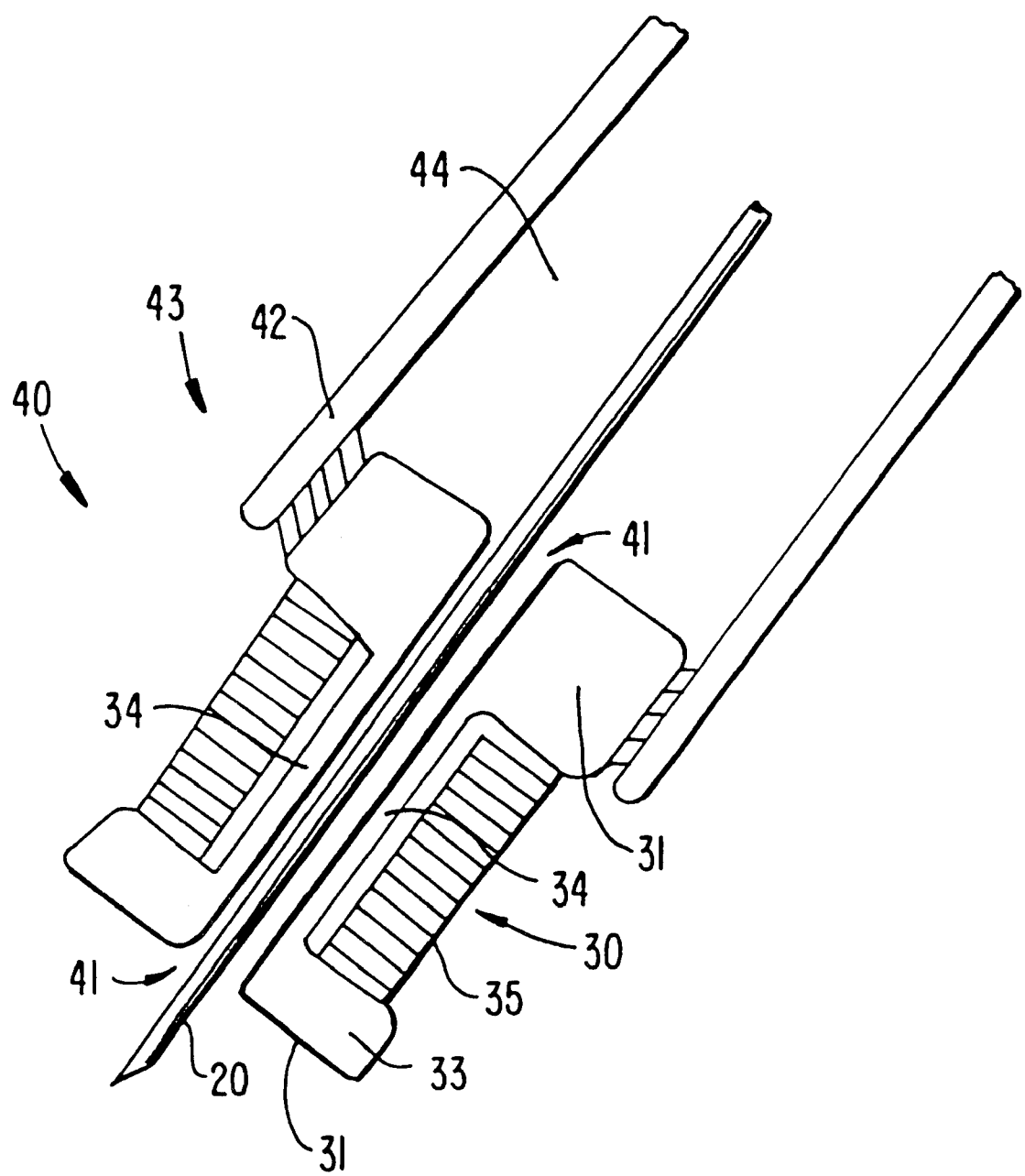
FIG. 3A is a sectional view of the distal tip of a device for enhancing cellular absorption of a substance delivered to a region of target tissue.

As is shown in FIG. 3A, the injection needle 20 of FIG. 1 and the vibrational energy emitter 30 of FIG. 2 can preferably be combined into an integrated device 40 which is preferably positioned at a distal end of a catheter 42. In a preferred embodiment, vibrational emitter 30 completely surrounds injection needle 20. An advantage of integrated device 40 is that a drug can be delivered to a target tissue region by way of injection needle 20 concurrently with the application of vibrational energy to the target region by emitter 30. As is seen in FIG. 3A, vibrational emitter 30 preferably comprises an inertial mass 31 and a head mass 33 with a piezostack 35 positioned therebetween. Inertial mass 31 and head mass 33 are preferably linked together by way of an internal rod 34 and the mass of radiating head 33 and the dimensions of piezostack 35 would be adjusted to achieve the final desired frequency and output displacement. Piezostack 35 would typically comprise on the order of twenty layers of ceramic material. Emitter 30 may alternatively include a piezoelectric tube, a magnetostrictive device, or transducer bars. Emission may be in either the forward or lateral directions.

Preferably, injection needle 20 is slidably received in lumen 44 of catheter 42 and in lumen 41 of emitter 30. As such, injection needle 20 can be easily advanced or withdrawn to project out of the distal end of emitter 30, as desired. For example, the distal end 42 of catheter 40 can first be safely introduced into a patient's body and positioned proximal a target tissue region. Subsequently, injection needle 20 can then be advanced to project out of the emitter 30 and into the target tissue, thereby delivering a drug or other substance to the target tissue.

Figure 3B:
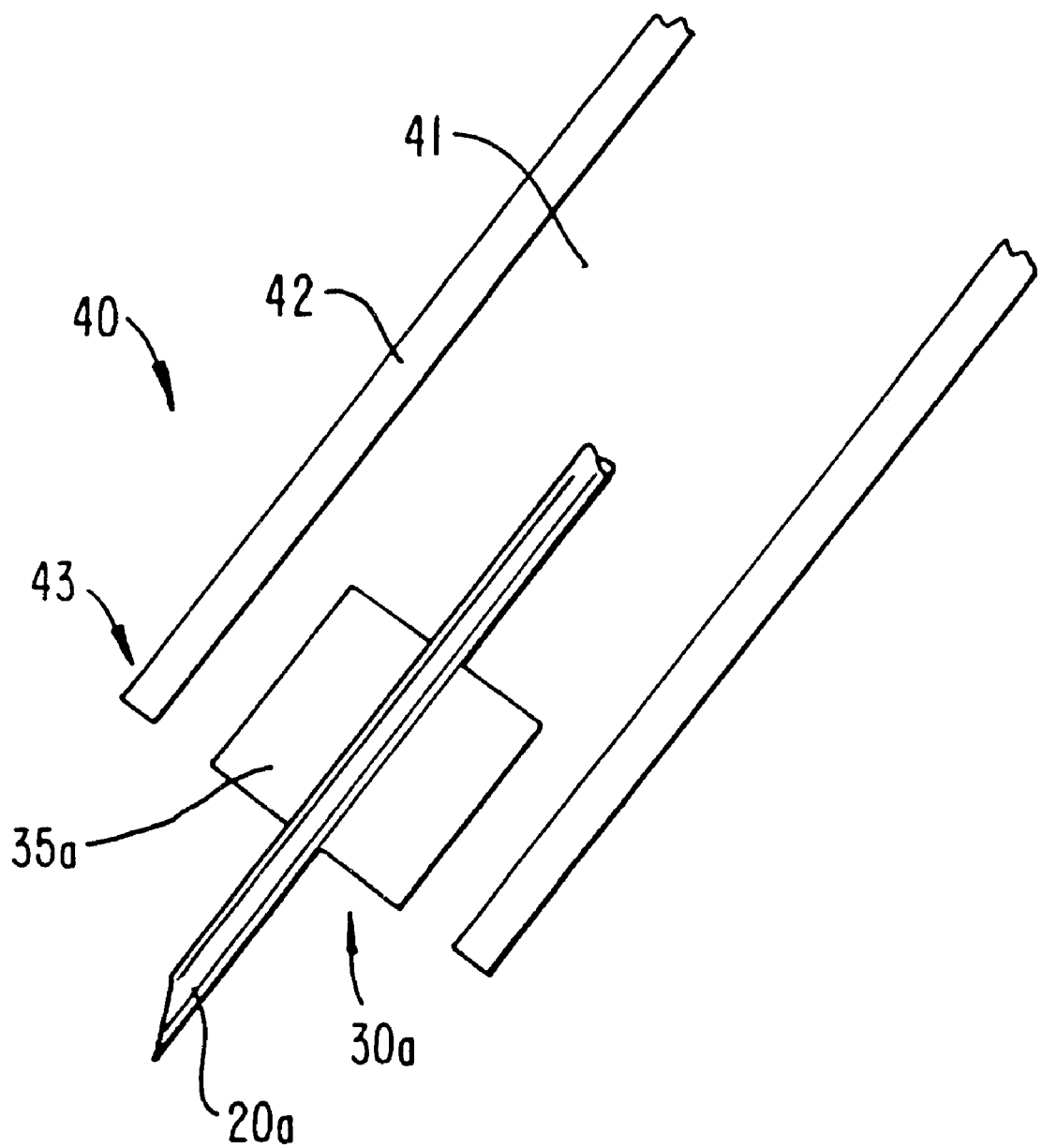
FIG. 3B is a sectional view of the distal tip of an alternate device for enhancing cellular absorption of a substance.

FIG. 3B shows an alternative embodiment corresponding to FIG. 3A, but with the injection needle 20a being connected directly to energy emitter 30a. Energy emitter 30a may comprise a piezostack 35a. Vibration of piezostack 35a causes needle 20a to vibrate. Needle 20a, being short and stiff in nature, will oscillate axially at the same frequency and at the same amplitude of the piezostack 35a. The tip of the needle 20a will thus act as an ultrasound emitter. An advantage of this device is that, as energy emitter 30a is attached to the substance delivery injection needle 20a, very effective application of ultrasound energy at the exact point of drug delivery is achieved. The present needle 20a is preferably fabricated from stainless steel, while the emitter is fabricated from piezoelectric material. This system is an improvement over prior developments because the needle 20a will thus oscillate at the site of injection causing formation of microbubbles as the liquid agent is injected. The presence of microbubbles enhances cavitation which improves the efficiency of transfections. Needle 20a will thus act as an extension of transducer 30a with the tip of the needle vibrating at the same frequency and amplitude as that of the transducer. Similar to the device of FIG. 3a, the device of FIG. 3B is preferably received in the system of catheter 40, as previously described.

Figure 3C:
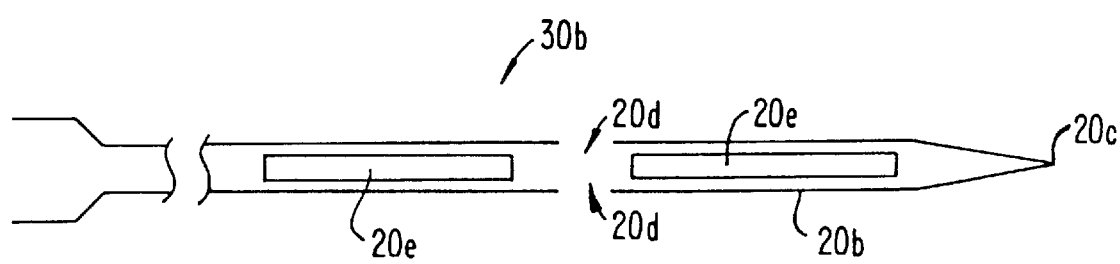
FIG. 3C is a section view of the distal tip of a third alternative device for enhancing cellular absorption of a substance.

FIG. 3C shows a third alternative embodiment of a device for enhancing cellular absorption of a substance comprising an integrated injection needle and ultrasound energy emitter system 30b. System 30b comprises an injection needle 20b having a penetration tip 20c and one or more portals 20d. Penetration tip 20c preferably has a 14–30 gauge diameter for easy skin penetration. One or more internally mounted transducers 20e are provided. Preferably, transducers 20e are located proximal and distal or just proximal or just distal the locations of portal or portals 20d. Accordingly, drug injection can be provided such that ultrasonic energy emitted by transducers 20e is adjacent to the point of drug delivery through portals 20d, thus ensuring that ultrasound energy is applied directly to the target tissue, thereby increasing drug delivery effectiveness into the target cells.

Figure 4:
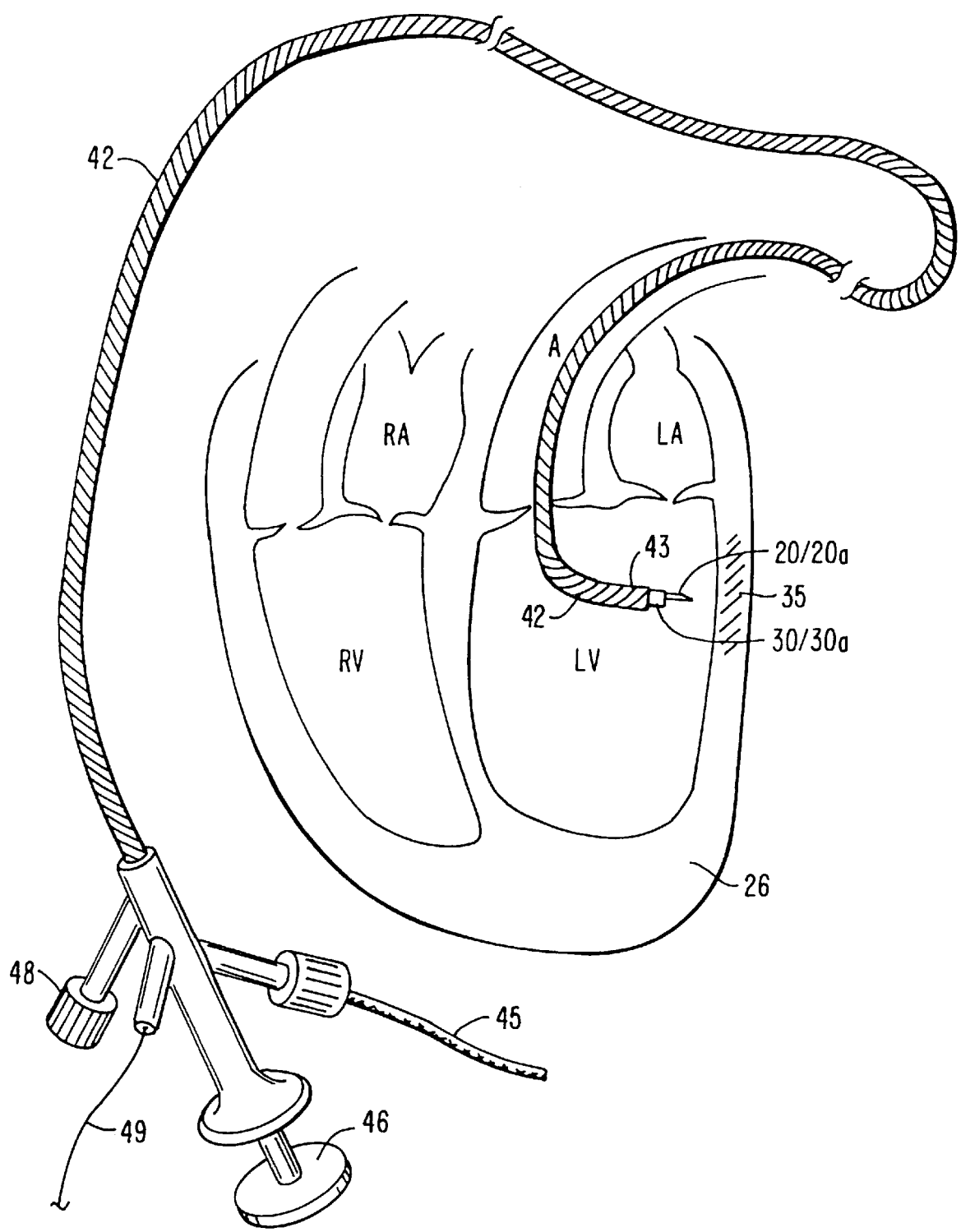
FIG. 4 is a pictorial view of the device of FIGS. 3A, 3B or 3C received into a ventricle of a patient's heart.

FIG. 4 is a pictorial view of a preferred embodiment of the device of FIG. 3A, 3B, or 3C as inserted into the left ventricle LV of a patient's heart with catheter 42 positioned proximate a diseased region 25 of a patient's myocardium 26. Catheter 42 is preferably provided with a guidewire 45, a distal tip deflection actuator 46 for controlling the position of distal end 43 of the catheter 42. A flush luer 48 is adapted to provide plumbing for contrast dye or for the irrigation of the guidewire lumen. Catheter 42 would preferably be rigid enough to allow for pushability and torqueability as required for typical intracardiac procedures. Electrical connectors 49 are also typically provided for powering emitter 30 and other transducers which will be described herein.

The internal guidewire 45 used to direct the distal tip 43 of catheter 42 would preferably be received in a separate lumen from that of injection needle 20/20a. However, it is to be understood that guidewire 45 may itself comprise injection needle 20 or 20a. Conceivably, however, guidewire 45 and injection needle 20/20a can both be received in the central lumen 44 with guidewire 45 first positioning distal head 43 of catheter 42. Subsequently, guidewire 45 would then be removed such that injection needle 20/20a can be slidably received in central lumen 44 such that injection needle 20/20a passes out of distal end 43 of catheter 42 to a location past vibration energy emitter 30 and into the target tissue.

In the preferred method of enhancing cellular absorption of a substance delivered into a patient's myocardial tissue, the first step is the positioning of distal end 43 of catheter 42 proximal diseased tissue region 25. The present invention comprises a variety of different preferred approaches to positioning distal end 43 of catheter 42 into the patient's myocardium. Specifically, FIG. 5A illustrates an approach through the endocardium, FIG. 5B illustrates an approach through a coronary artery, FIG. 5C illustrates an open chest procedure approach through the epicardium, and FIG. 5D illustrates an approach wherein the needle and ultrasonic source are separated, and wherein the needle approaches through the endocardium with the ultrasonic emission originating from a transesophageal device or a transthoracic device.

Figure 5A:
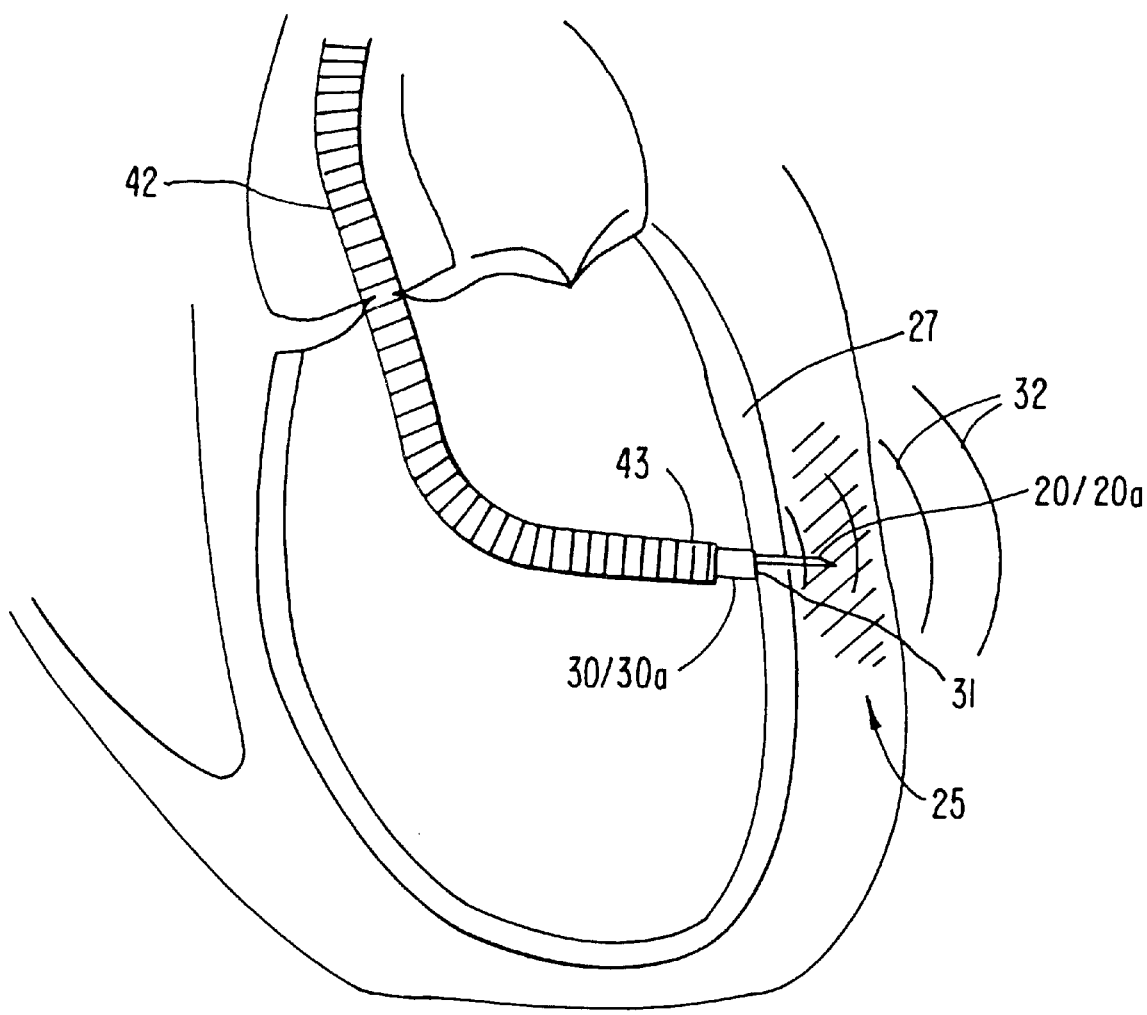
FIG. 5A is an enlarged pictorial view of the device of FIGS. 3A, 3B, 3C, and 4 shown penetrating through a patient's endocardium into the patient's myocardium.

As is shown in FIG. 5A, needle 20/20a is extended through the patient's endocardium 27 to penetrate into diseased region 25 and a fluid suspension containing the substance to be delivered is then passed into target region 25 by injection needle 20/20a. The energizing of transducer 30/30a generates ultrasound waves 32 which cause the tissue in target region 25 to vibrate by an amount sufficient to enhance absorption of the injected substance into this tissue. Preferably, planar vibrational surface 31 will be positioned in flush contact to endocardium 27, thereby providing optimal vibration energy transfer and controlling the penetration depth of injection needle 20/20a.

Figure 5B:
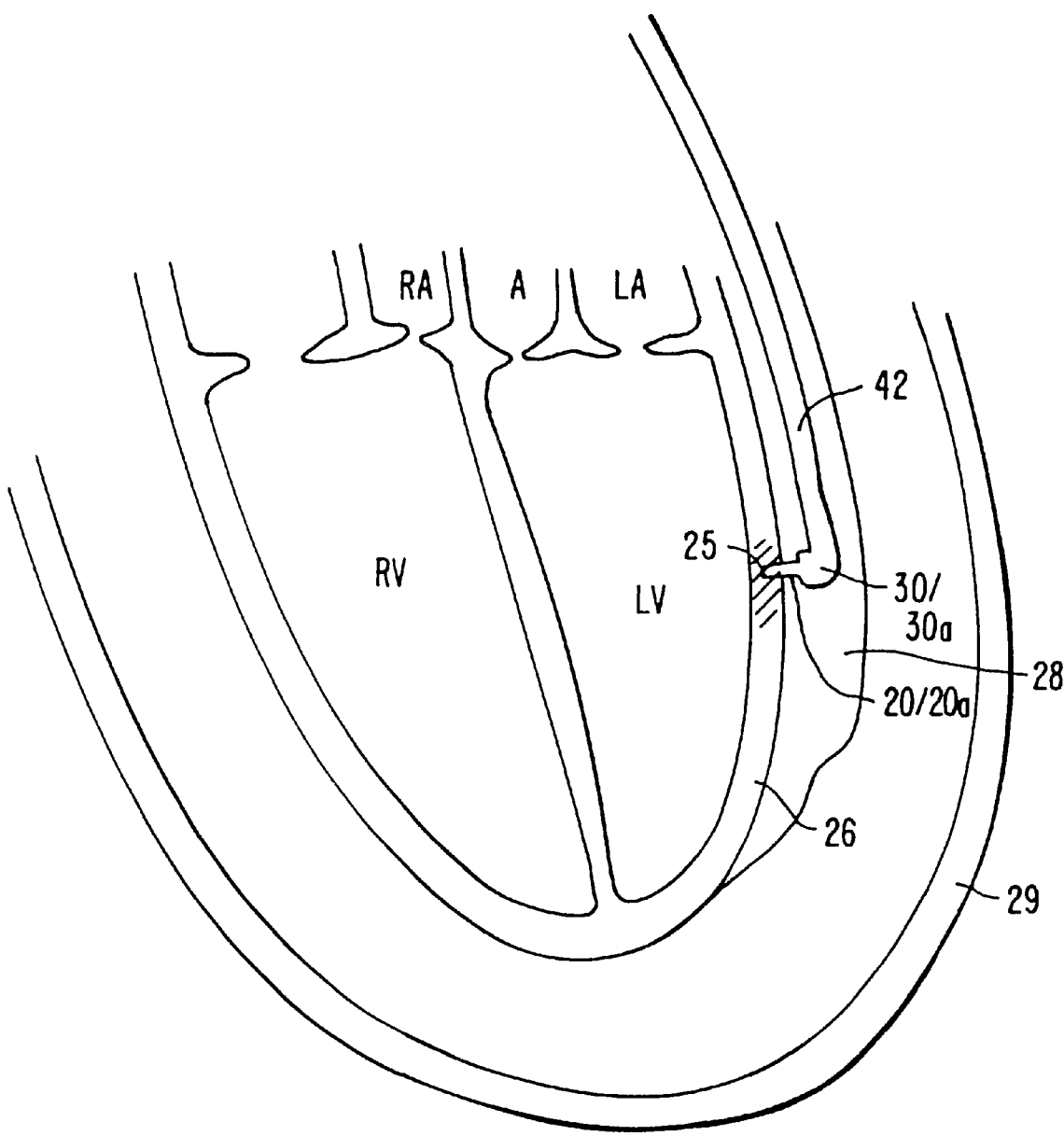
FIG. 5B is an enlarged pictorial view of the device of FIGS. 3A, 3B, 3C, and 4 shown penetrating through the wall of a patient's coronary artery and into the patient's myocardium.

As is shown in FIG. 5B, access to myocardium 26 can also be achieved with catheter 42 positioned intravascularly in coronary artery 28 with injection needle 20/20a passing through the arterial wall and into myocardium 26.

Figure 5C:
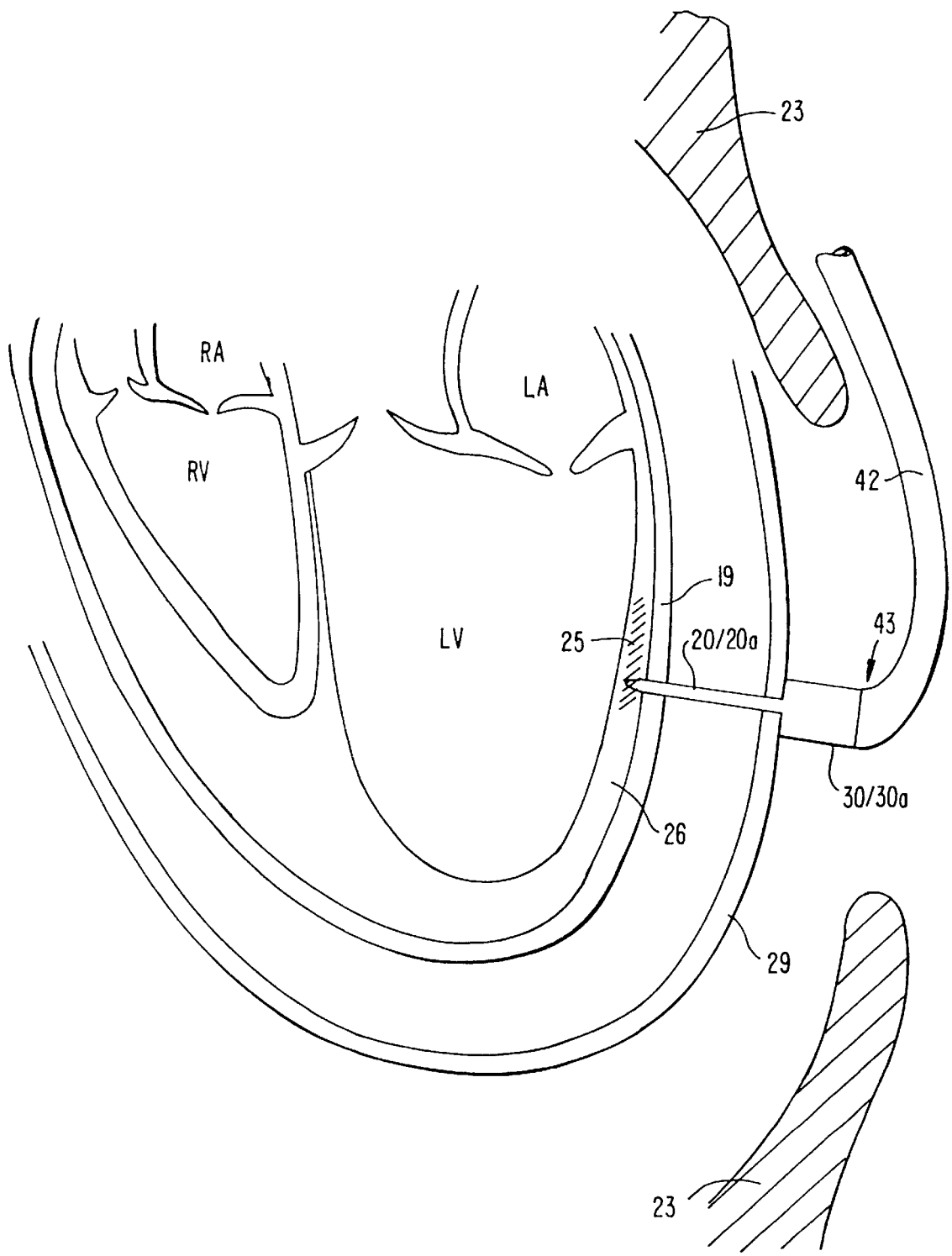
FIG. 5C is an enlarged pictorial view of the device of FIGS. 3A, 3B, 3C, and 4 shown penetrating through a patient's epicardium and into the patient's myocardium, via an open thoracotomy surgical approach.
Figure 5D:
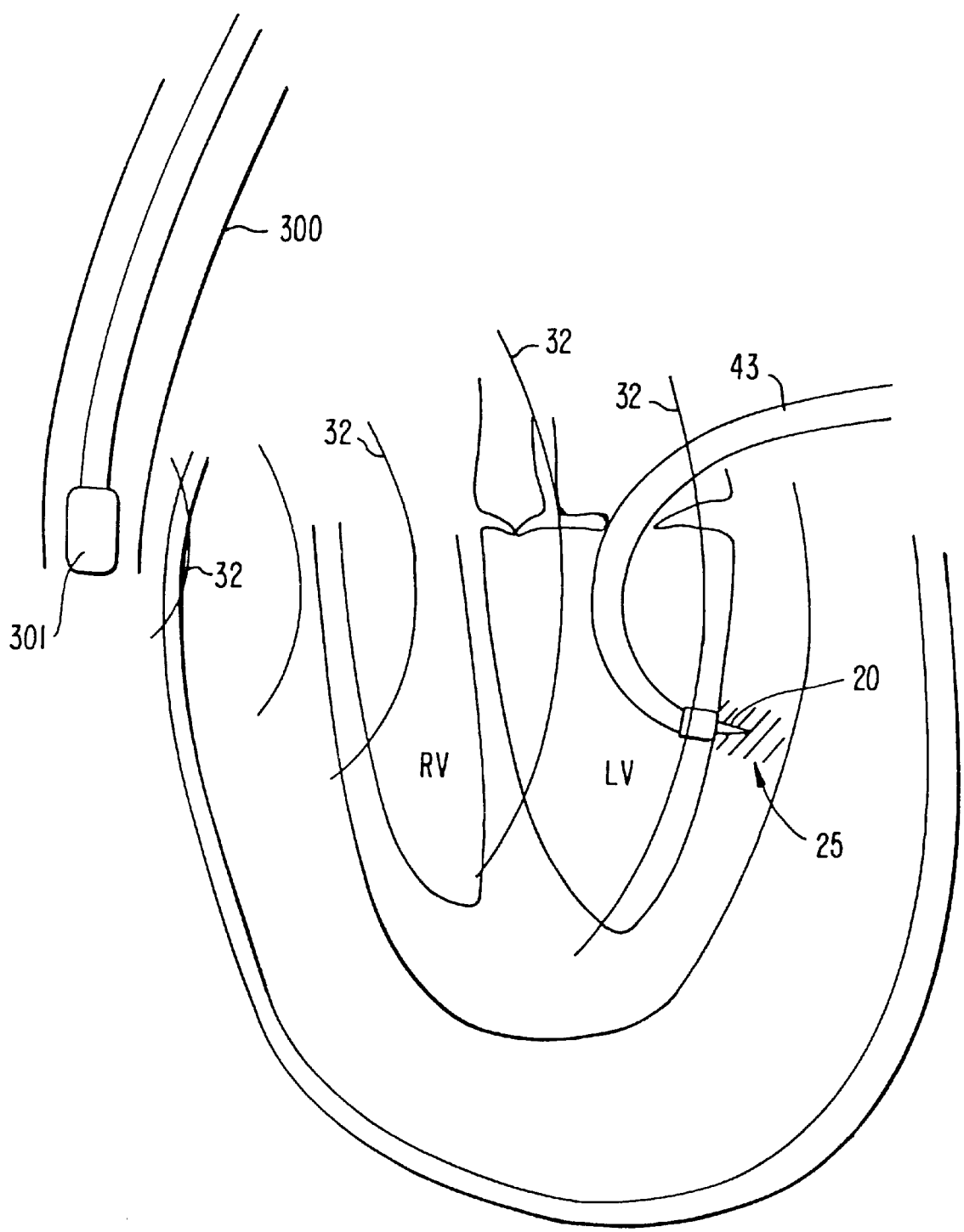
FIG. 5D is an enlarged pictorial view of needle injection of a drug with remote, simultaneous ultrasonic enhancement.

As is shown in FIG. 5C, access to myocardium 26 can also be achieved with device 42 positioned in or over the patient's pericardium 29 with injection needle 20/20a passing through epicardium 19. This approach may be accomplished in surgical procedures in which access to the patient's heart is achieved either through the sternum or between the ribs 23.

As is shown in FIG. 5D, access to the myocardium is achieved by the system depicted in FIG. 5A. It is to be understood, however, that access to the myocardium could also be achieved by the systems depicted in FIG. 5B or 5C. As depicted in FIG. 5D, the source of ultrasonic emission, however, is separated from the substance delivery system such that the ultrasonic energy may be emitted in the esophagus 300 from a large aperture focused transducer 301 or transducer array on a transducer array on a transesophagous probe assembly 302. Acoustic waves 32 may be divergent or focussed on a small spot consistent with the resolution of the ultrasonic emitter device.

Figure 6A:
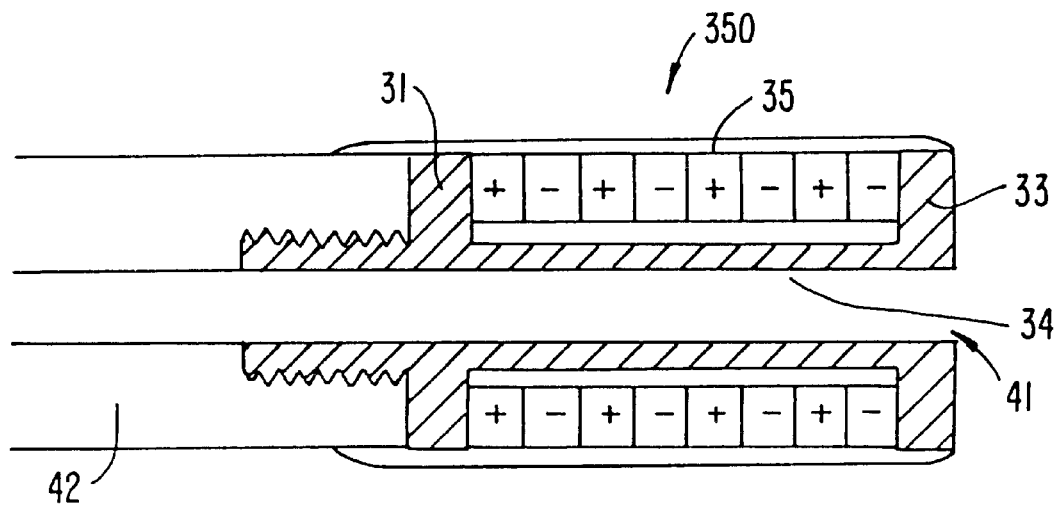
FIG. 6A is a side elevational sectional view of a first embodiment of the vibrational energy emitter of the device of FIG. 3A.
Figure 7:
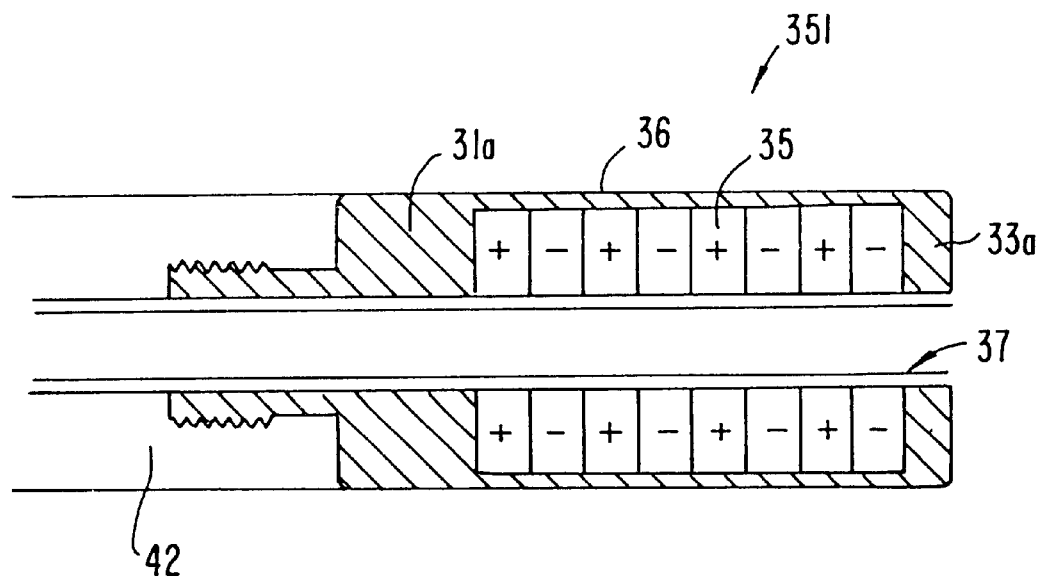
FIG. 7 is a side elevational sectional view of an alternative embodiment of the vibrational energy emitter of FIG. 6A.

FIG. 6A shows a sectional view of vibration energy emitter 30 as was shown in FIG. 3A. FIG. 7 shows an embodiment of a vibration emitter $30_1$ in which head mass 33a and inertial mass 31a are held together by a outer external casing or tensioning skin 36. An internal insulator 37 is provided as a conduit for an injection needle.

Figure 8:
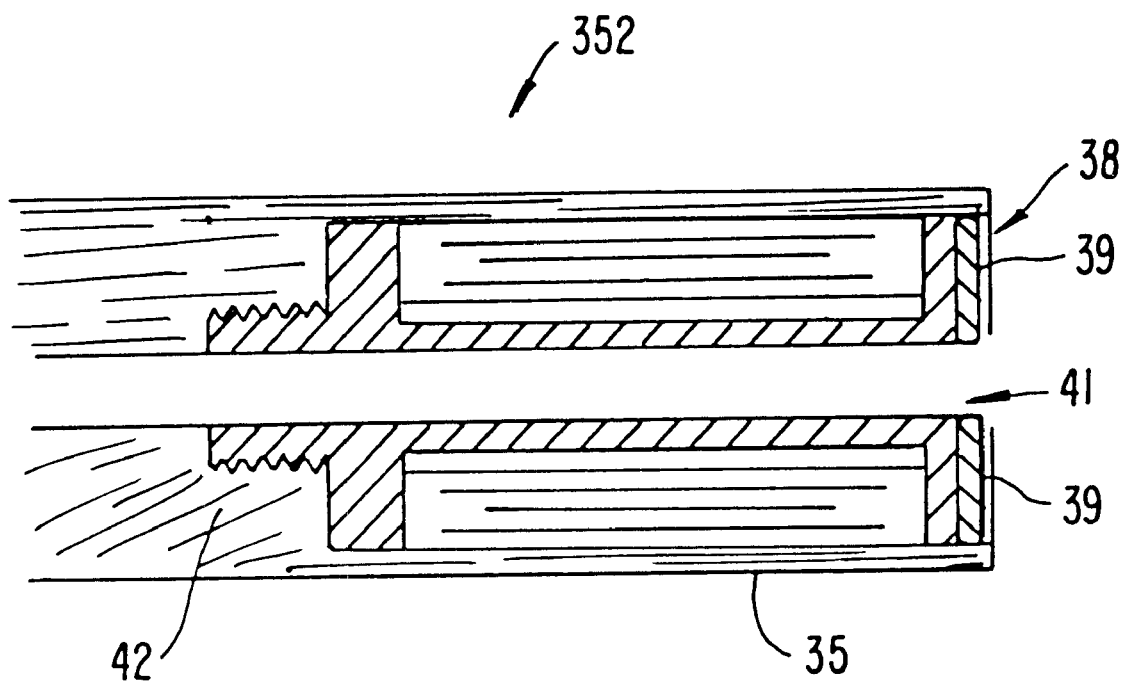
FIG. 8 is a side elevational sectional view of the vibrational emitter of FIG. 6A with an echo ranging transducer and electrophysiology electrode at its distal end.
Figure 9:
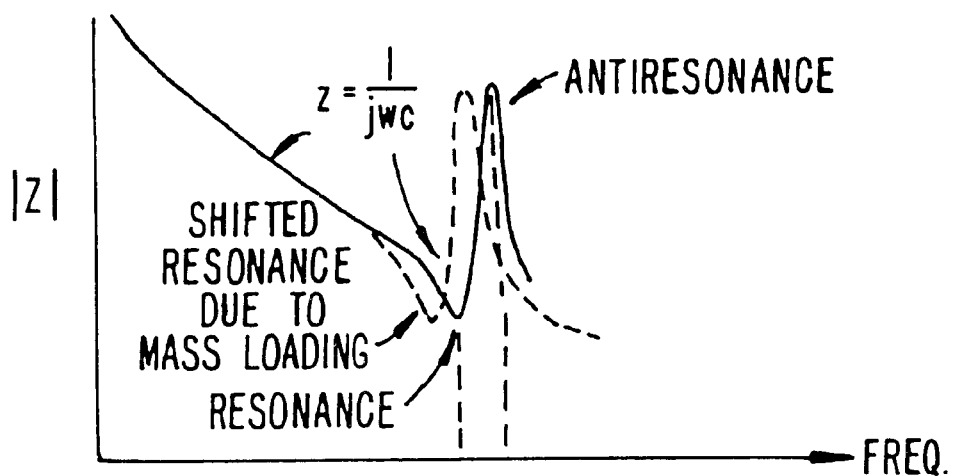
FIG. 9 is a representation of the electromechanical impedance magnitude of the vibrational device in contact with fluid and with the myocardium.
Figure 10:
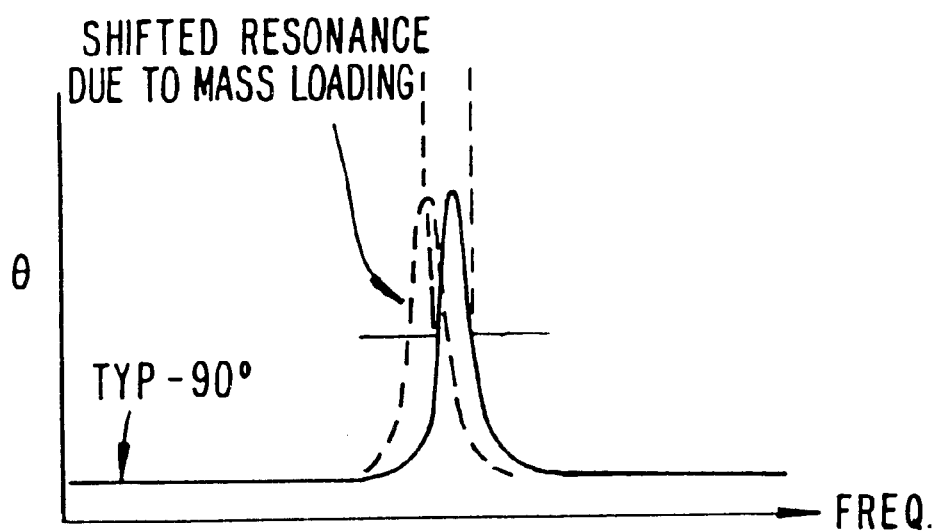
FIG. 10 is a representation of the electromechanical impedance phase angle of the vibrational device in contact with fluid and with the myocardium.

In an alternative embodiment, vibration energy emitter $30_2$, as shown in FIG. 8, further includes an echo ranging transducer 39 which is used to detect contact with the target tissue. Using this embodiment of the present invention in a preferred method, contact with the target tissue is confirmed by observing a change in the impedance of the ranging transducer 39. When ranging transducer 39 contacts the myocardial wall, the additional rigidity of the tissue typically pulls down the resonant frequency of the transducer by as much as 5%. As is illustrated in FIG. 9, this effect can easily be measured, and it can be used to affirm direct contact between ranging transducer 39 and the myocardial wall. FIG. 10 shows the corresponding impedance phase shift as ranging transducer 39 contacts the myocardial wall. As can be seen, this effect can also be easily measured.

An electrical lead 38, positioned over then distal face of the transducer as shown in FIG. 8, can be used for electrocardiograph monitoring which permits the electrocardiograph function to be traced and mapped onto commercially available electrophysiological equipment such that the location of a specific lesion in the myocardium can be precisely determined, thereby allowing the drug delivery system at the distal end of the catheter to be guided to an optimal location for drug delivery. Alternatively, electrical lead 38 can be in the form of band wrapped around the circumference of the distal end of the catheter and can be used for electrophysiology.

Figure 11:
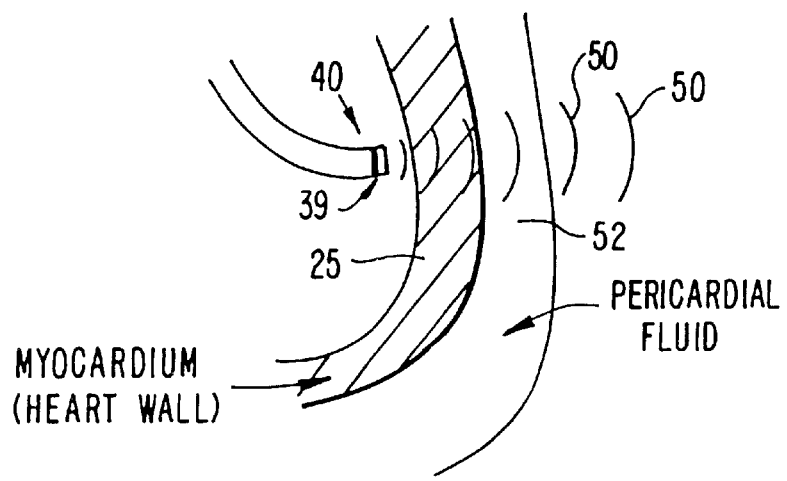
FIG. 11 is a pictorial representation of the range finding transducer emitting a signal into the myocardium.

As shown in FIG. 11, ranging transducer 39 can also be used to measure the thickness of the myocardium, as follows. As the tip of catheter 40 approaches the endocardium, ranging transducer 39 is repetitively pulsed in a pulse echo, or A-scan mode. Ultrasound waves 50 will reflect off of the tissue, creating echoes which return to ranging transducer 39. The amplitude and duration of the returning echoes are determined by the acoustic impedance of the tissue and its thickness.

Figure 12:
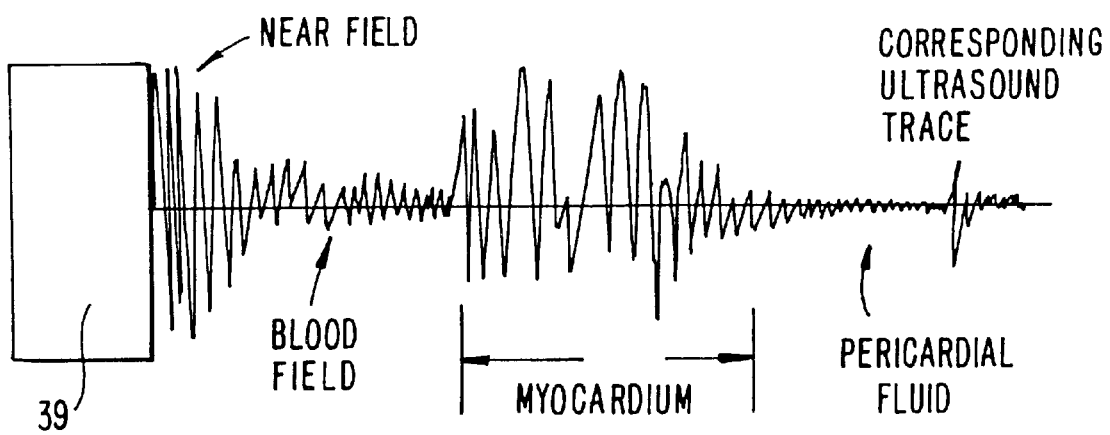
FIG. 12 is a representation of the return echo from the range finding transducer's emitted pulse, shown coming back from the myocardium.

As shown in FIG. 12, which represents the amplitude and duration of the ultrasound echo, the distance from the ranging transducer 39 to the myocardium surface is represented by a low amplitude blood field echo. The myocardium presence is represented by a high amplitude echo, the duration of which is proportional to its thickness, and the pericardial fluid is represented by a low amplitude echo. Accordingly, measurements can be easily made to determine the thickness of the myocardium. The ranging transducer and therapy transducers may be separate piezoelectric ceramic devices, although electrode patterning may allow the use of a single component.

As the operator moves the present device from site to site making multiple injections and applying vibrational energy, the echo ranging transducer 39 would first ascertain whether direct contact has been made with the myocardial wall. Thereafter, transducer 39 could be used to determine the wall thickness such that the proper depth setting for the injection needle plunge could be determined. Doppler signal processing of the A-mode traces 50 might further help delineate the margin. Software may then compute the thickness of the myocardium.

Figure 6B:
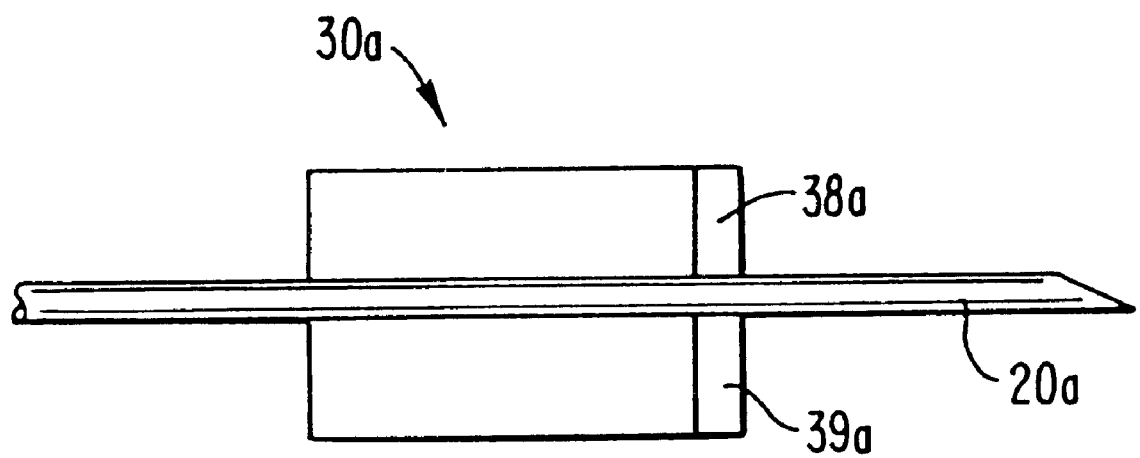
FIG. 6B is a side elevational sectional view of a combined vibrational energy emitter and injection device of FIG. 3B.

FIG. 6B shows a sectional view of vibration energy emitter 30a as was shown in FIG. 3B, having a ranging transducer 39a and electrical lead 38a positioned thereon, operating similar to ranging transducer 39 and electrical lead 38, described herein.

Figure 13:
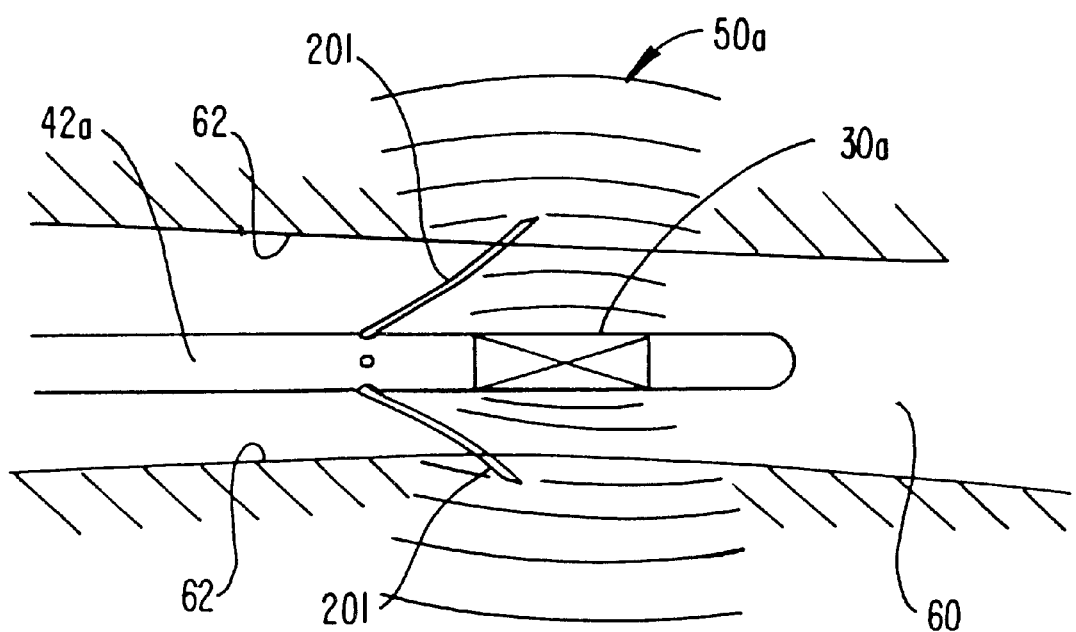
FIG. 13 is a pictorial representation of an alternative embodiment of a device for enhancing cellular absorption having a vibrational energy emitter and plurality of radially outwardly extending retractable injection needles.

In yet another embodiment of the present device, as illustrated in FIG. 13, catheter 42a is received into a intraluminal cavity 60. Intraluminal cavity 60 can either be a naturally occurring cavity in a patient's body or a cavity formed by injection of a needle into the patient's body. A drug or other substance is delivered into a target region of tissue by puncturing cavity wall 62 of intraluminal cavity 60 by injection needles $20_1$. Preferably, injection needles $20_1$ are disposed to extend radially outward from catheter 42a as shown. In addition, injection needles 20a are preferably retractable into catheter 42a such that in a preferred method, catheter 42a can first be conveniently inserted into lumen 60, and subsequently, injection needles $20_1$ can then be radially extended such that they puncture wall 62 at a variety of radial locations. This radial puncturing of the wall of the interluminal cavity would operate to center catheter 42a within the intraluminal cavity 60. In this embodiment, vibrational energy emitter 30a would emit vibrational energy radially outward as shown by ultrasonic waves 50a. Fluoroscopic imaging may be used to define a luminal diameter and allow the preferred setting of vibrational energy per the observed distance between the catheter 42a to wall 62.

Figure 15:
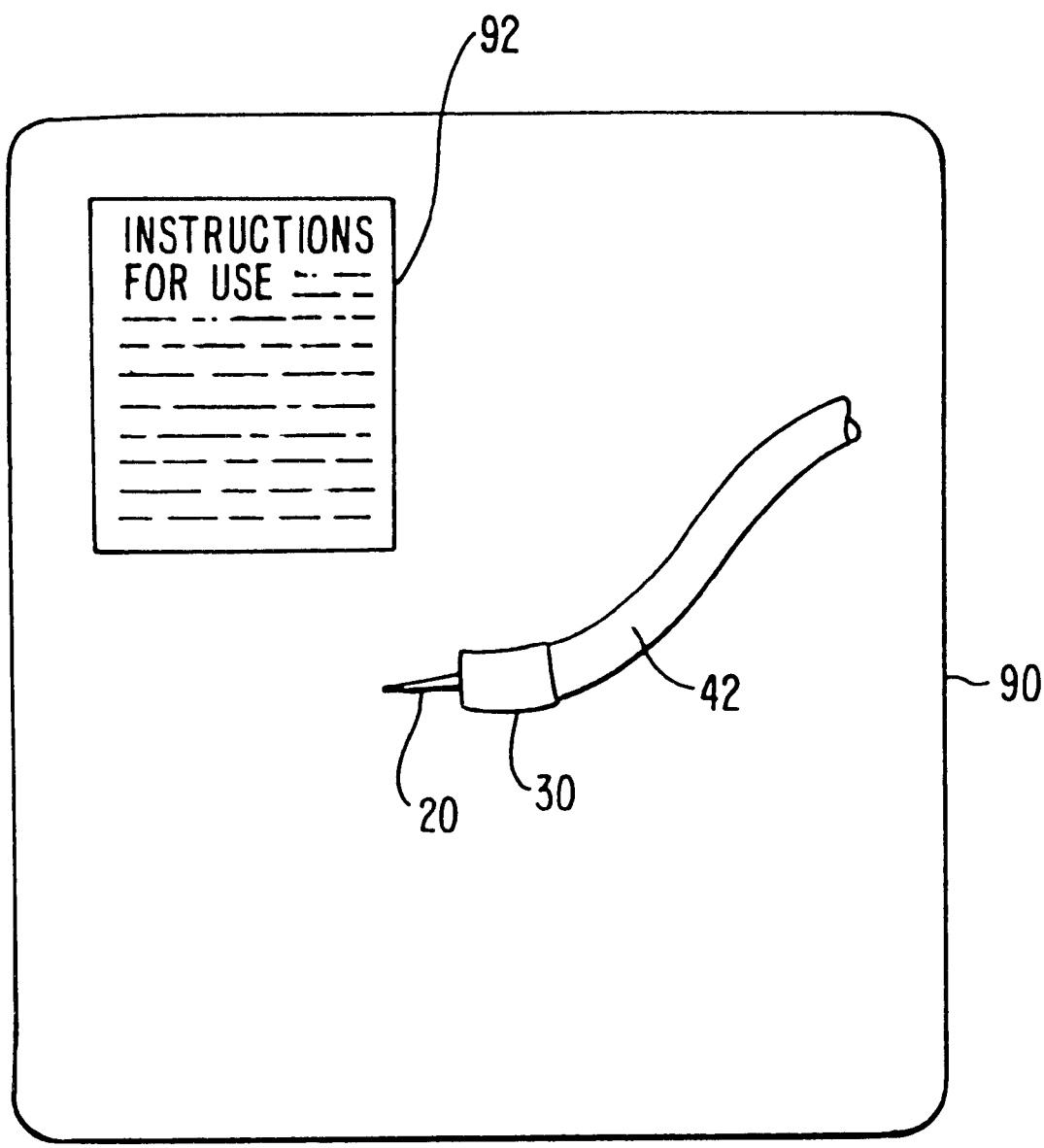
FIG. 15 is an illustration of a kit comprising devices for enhancing cellular absorption and instructions for its use.

The present invention also includes a kit 90, as seen in FIG. 15, which includes any of the preferred systems for enhancing cellular absorption of a substance as described herein, for example, a catheter 42 having an ultrasonic emitter 30/30a and an injection needle 20/20a, as has been described. Also included in kit 90 are instructions for use 92 which may be in the form of literature accompanying the system, writing on packaging material, information stored on video or audio discs, electromagnetic data storage formats, or other data storage and presentation media. Instructions for use 92 set forth any of the preferred methods described herein.

Figure 14:
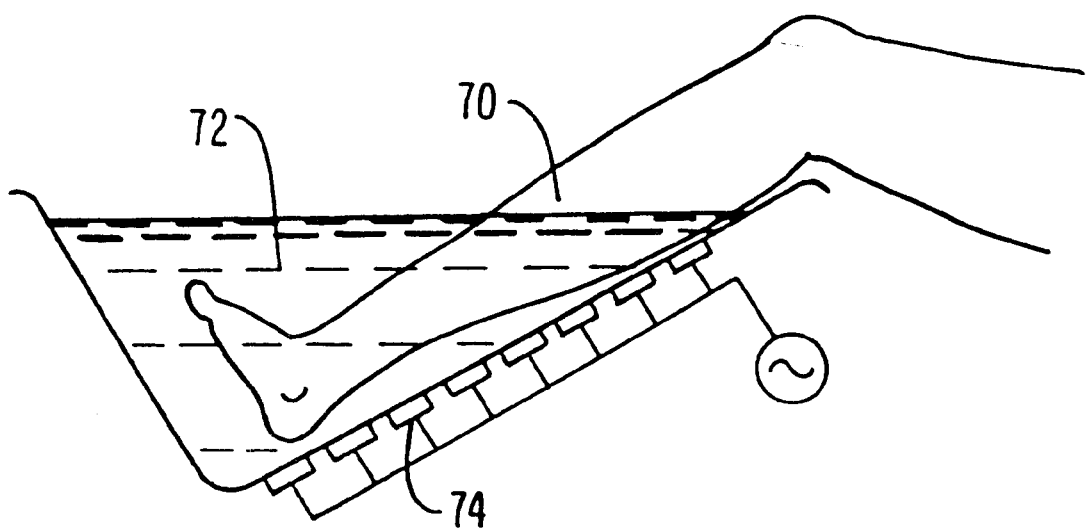
FIG. 14 is a pictorial representation of a patient's leg immersed in a fluidic environment which is subjected to vibrational energy.

In another aspect of the present invention, as seen in FIG. 14, a patient's leg 70 is received into a fluidic bath 72. A plurality of ultrasonic vibrational energy emitters 74 are provided to subject the fluidic bath to ultrasonic vibrational energy. The apparatus shown in FIG. 14 is particularly useful for patients requiring treatment for vascular problems in the leg. In a preferred method, a series of multiple injections are typically made in the patients leg from just below the knee to the ankles. The apparatus of FIG. 14 then permits the entire leg or arm of the patient to be subjected to an ultrasonic environment, with the ultrasound vibrations enhancing the cellular absorption of a drug or other substance into the arm or leg. An advantage of this apparatus is that a large area of the patient's body can be subjected to ultrasound without the problems of acoustic beam spreading and unwanted amplification, as follows.

Sharply focusing an acoustic beam at a target tissue region substantially amplifies the acoustic power at any point, but then the beam will need to be swept back and forth over the entire surface area to achieve therapeutic levels over a large volume of tissue. This sweeping may require an unacceptable amount of time. To eliminate the need for such sweeping, the acoustic beam might be defocussed to provide acoustic energy over a large volume, at a lower power level. As such, unacceptable amplification of the vibrational energy would be required.

A fluidic environment will transmit ultrasonic energy more readily than a gaseous environment. Accordingly, with the present invention, the use of fluidic bath 72 will overcome the problem of acoustic beam spreading which would have required the beam to be focused and amplified at any particular location in the leg. As such, the problem of topical administration of ultrasound is overcome.

Figure 16:
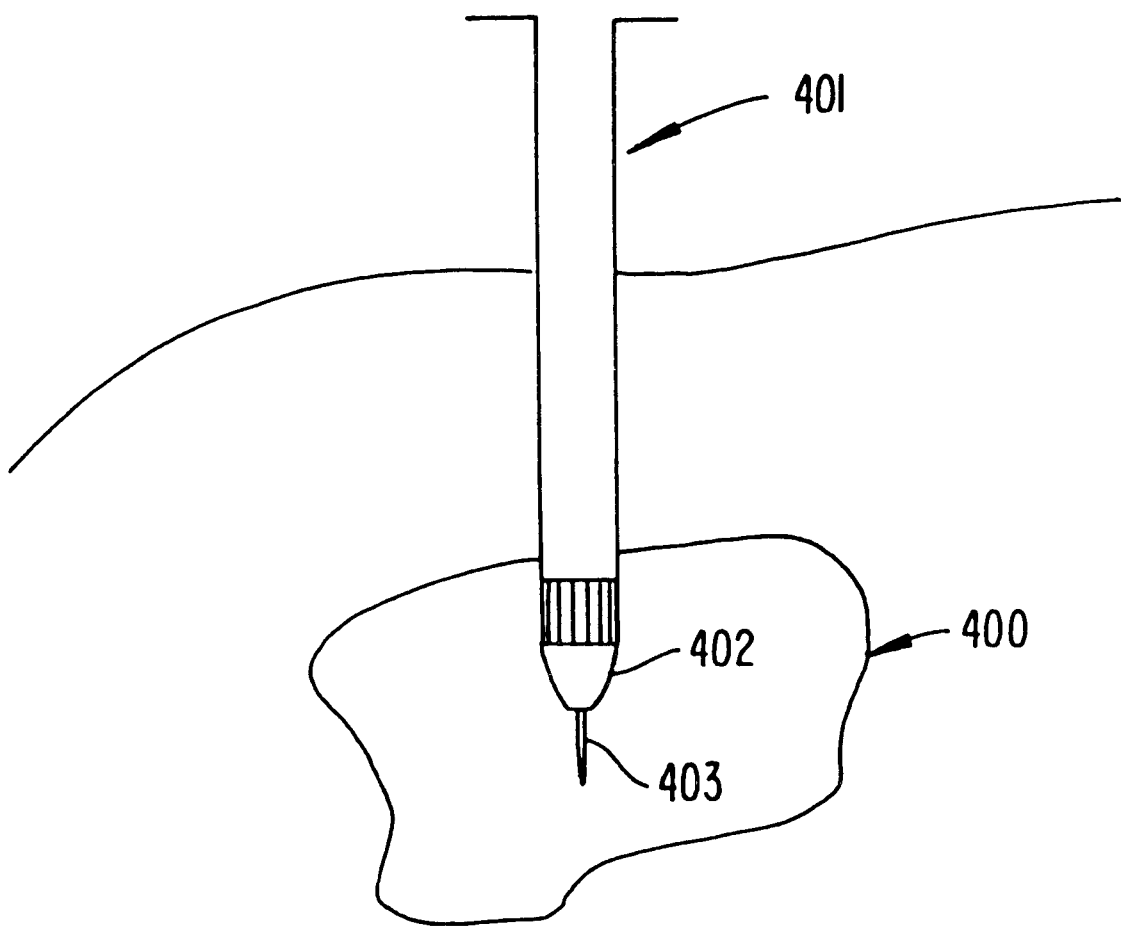
FIG. 16 is an illustration of treatment of soft tissue lesions by combined needle injection and ultrasonic emission.

In another aspect of the present invention, needle injection and sonication can be applied in man made lumens within the body, such as those depicted in FIG. 16 for treating soft tissue lesions 400. A semirigid tube 401 similar to the catheter configuration previously described is inserted into the subject's body, and directly into the lesion side, by conventional clinical techniques. Semirigid tube 401 contains ultrasonic emission surfaces 402 at it's distal tip and an injection needle 403 also protruding from it's distal tip. This technique can be useful for treating typically cancerous lesions of the brain, breast or liver.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method of enhancing cellular absorption of a substance delivered into a target region of a patient's body, comprising:
    (a) injecting the substance into solid tissue in the target region; and
    (b) directing vibrational energy to the target region, said vibrational energy having a Mechanical Index in the range of 0.3 to 15 and having a Thermal Index of less than 4.0, said vibrational energy being of a type and in an amount sufficient to enhance absorption into cells of the target region.

2. The method of enhancing cellular absorption of a substance as in claim 1, wherein,
    said target region is in the myocardium.

3. The method of enhancing cellular absorption of a substance as in claim 2, wherein said injecting step comprises injection through the epicardium.

4. The method of enhancing cellular absorption of a substance as in claim 2, wherein said injecting step comprises injection through the endocardium.

5. The method of enhancing cellular absorption of a substance as in claim 2, wherein,
    said substance promotes angiogenesis.

6. The method of enhancing cellular absorption of a substance as in claim 5, wherein,
    said substance is selected from the group consisting of VEGF and BFGF.

7. The method of enhancing cellular absorption of a substance as in claim 5, wherein,
    said substance inhibits restenosis.

8. The method of enhancing cellular absorption of a substance as in claim 5, wherein,
    said substance is eNOS.

9. The method of enhancing cellular absorption of a substance as in claim 2, wherein,
    said substance prevents congestive heart failure.

10. The method of enhancing cellular absorption of a substance as in claim 2, wherein,
    said substance is selected from the group consisting of brain naturatic peptides and beta-andrenogenic receptors.

11. The method of enhancing cellular absorption of a substance as in claim 2, wherein,
    said substance is a DNA-based vaccine.

12. The method of enhancing cellular absorption of a substance as in claim 1, wherein, the step of injecting the substance is performed at least partly after the step of directing vibrational energy to the target region.

13. The method of enhancing cellular absorption of a substance as in claim 1, wherein, said vibrational energy has a frequency range of 20 kHz to 3.0 MHz.

14. The method of enhancing cellular absorption of a substance as in claim 1, wherein, absorption is increased by at least about 5% relative to uptake in the absence of the vibrational energy.

15. The method of enhancing cellular absorption of a substance as in claim 14, wherein, absorption is increased by at least about 5000% relative to uptake in the absence of the vibrational energy.

16. The method of enhancing cellular absorption of a substance as in claim 1, wherein the step of directing vibrational energy to the target region comprises:

engaging a vibrational surface against tissue of the target region.

17. The method of enhancing cellular absorption of a substance as in claim 16, wherein the vibrational surface is generally planar and engaged against an external surface of a patient's skin, organ, or tissue.

18. The method of enhancing cellular absorption of a substance as in claim 16, wherein the vibrational surface is a probe that penetrates into tissue in the target region.

19. The method of enhancing cellular absorption of a substance as in claim 18, wherein the probe is a needle used for injecting the substance into the target region.

20. The method of enhancing cellular absorption of a substance as in claim 17, wherein the needle vibrates to form microbubbles, thereby enhancing cavitation at the target region.

21. The method of enhancing cellular absorption of a substance as in claim 1, wherein the step of directing vibrational energy to the target region comprises:

generating a ultrasound beam external to the patient; and
directing the ultrasound beam to the target region.

* * * * *